(12) United States Patent
Chimile

(10) Patent No.: US 12,151,043 B2
(45) Date of Patent: Nov. 26, 2024

(54) KEYPAD STERILIZATION ASSEMBLY

(71) Applicant: Ryan Chimile, E Beaver Falls, PA (US)

(72) Inventor: Ryan Chimile, E Beaver Falls, PA (US)

( * ) Notice: Subject to any disclaimer, the term of this patent is extended or adjusted under 35 U.S.C. 154(b) by 690 days.

(21) Appl. No.: 17/504,673

(22) Filed: Oct. 19, 2021

(65) Prior Publication Data
US 2023/0118875 A1    Apr. 20, 2023

(51) Int. Cl.
*A61L 2/22* (2006.01)

(52) U.S. Cl.
CPC .............. *A61L 2/22* (2013.01); *A61L 2202/14* (2013.01); *A61L 2202/15* (2013.01)

(58) Field of Classification Search
CPC .......... A61L 2/18; A61L 2/22; A61L 2202/15; A61L 2202/14
See application file for complete search history.

(56) References Cited

U.S. PATENT DOCUMENTS

| | | | |
|---|---|---|---|
| 8,481,970 B2 | 7/2013 | Cooper | |
| 11,559,596 B2* | 1/2023 | Harris | E05B 1/0069 |
| 11,897,515 B2* | 2/2024 | McKnew | G06Q 50/40 |
| 12,097,298 B1* | 9/2024 | Ashmore | A61L 2/26 |
| 2002/0133900 A1* | 9/2002 | Perkins | B08B 5/04 15/320 |
| 2011/0291995 A1 | 12/2011 | Shr | |
| 2012/0240968 A1 | 9/2012 | Schumacher | |
| 2013/0200279 A1 | 8/2013 | Chuang | |
| 2014/0252247 A1 | 9/2014 | Moskowitz | |
| 2017/0333582 A1* | 11/2017 | Davis | A61L 2/24 |

FOREIGN PATENT DOCUMENTS

WO    WO2013185233    12/2013

* cited by examiner

*Primary Examiner* — Shogo Sasaki

(57) ABSTRACT

A keypad sterilization assembly includes a keypad that has a plurality of keys is movably integrated therein. The plurality of keys can be manipulated for entering an alphanumeric code. A fluid port is coupled to the keypad and a reservoir is fluidly attachable to the fluid port. The reservoir contains an anti-bacterial solution. A pair of nozzles is provided and each of the nozzles is coupled to the keypad. Each of the nozzles is directed toward the plurality of keys and each of the nozzles is in fluid communication with the fluid port. Additionally, each of the nozzles sprays a measured amount of the anti-bacterial solution onto the keys to sterilize the keys.

6 Claims, 5 Drawing Sheets

KEYPAD STERILIZATION ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to sterilization devices and more particularly pertains to a new sterilization device for sterilizing a keypad. The device includes a keypad, a reservoir that is removably coupled to the keypad, a pump and a plurality of nozzles. The reservoir contains an anti-bacterial solution that can be sprayed outwardly from the nozzles. In this way the anti-bacterial solution sterilizes the keypad to inhibit the transmission of infectious bacterial diseases between people that employ the keypad.

(2) Description of Related Art Including Information Disclosed Under 37 CFR 1.97 and 1.98

The prior art relates to sterilization devices including a variety of sterilizing devices that includes an ultraviolet light emitter for sterilizing a variety of objects. The prior art discloses a sanitizing device that includes a well for receiving a hand and a plurality of sprayers for spraying hand sanitizer on the hand. In no instance does the prior art disclose a keypad that includes a reservoir and nozzles for spraying an anti-bacterial solution onto the keypad for sterilizing the keypad.

BRIEF SUMMARY OF THE INVENTION

An embodiment of the disclosure meets the needs presented above by generally comprising a keypad that has a plurality of keys is movably integrated therein. The plurality of keys can be manipulated for entering an alpha-numeric code. A fluid port is coupled to the keypad and a reservoir is fluidly attachable to the fluid port. The reservoir contains an anti-bacterial solution. A pair of nozzles is provided and each of the nozzles is coupled to the keypad. Each of the nozzles is directed toward the plurality of keys and each of the nozzles is in fluid communication with the fluid port. Additionally, each of the nozzles sprays a measured amount of the anti-bacterial solution onto the keys to sterilize the keys.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
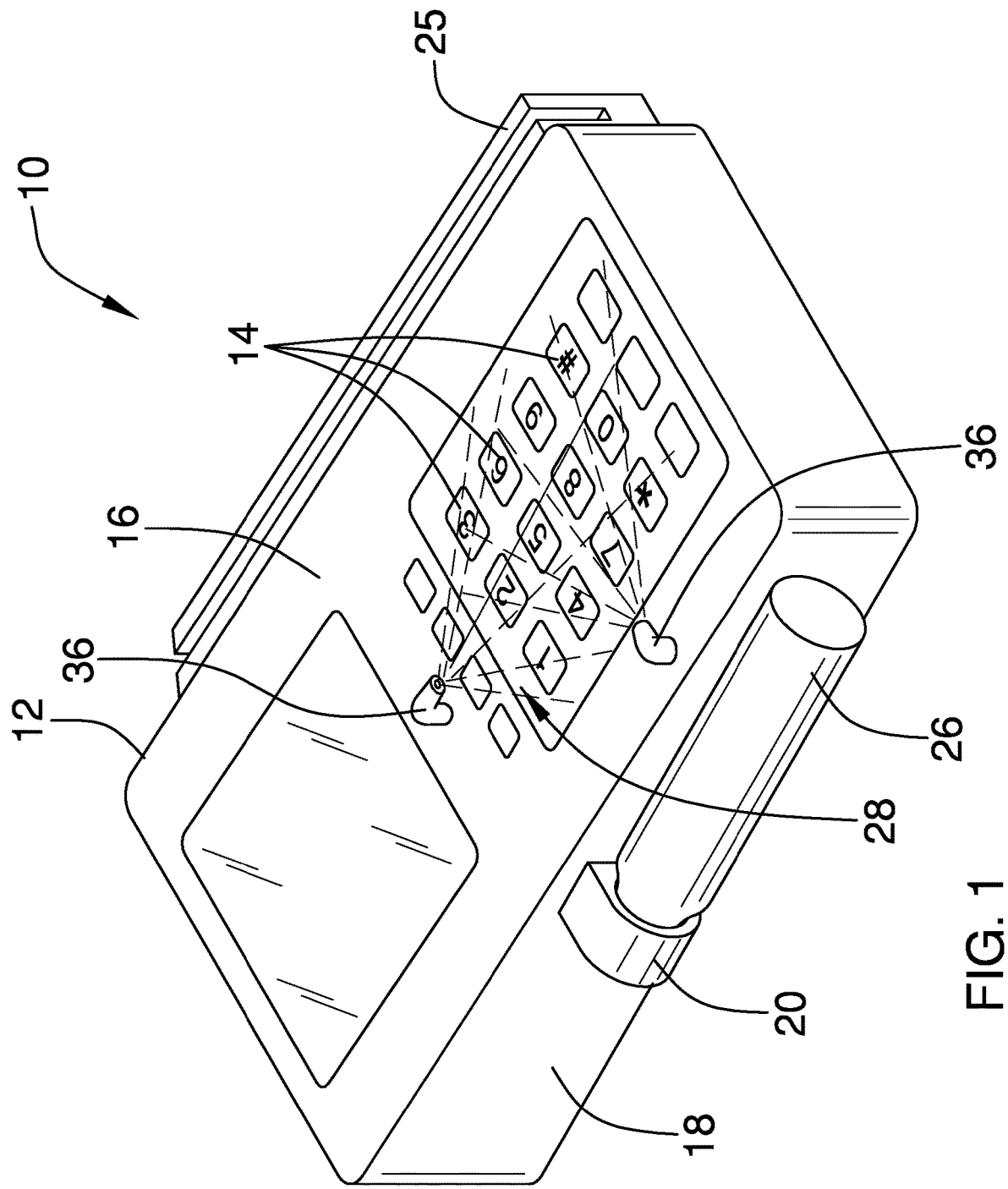
FIG. 1 is a perspective view of a keypad sterilization assembly according to an embodiment of the disclosure.
Figure 2:
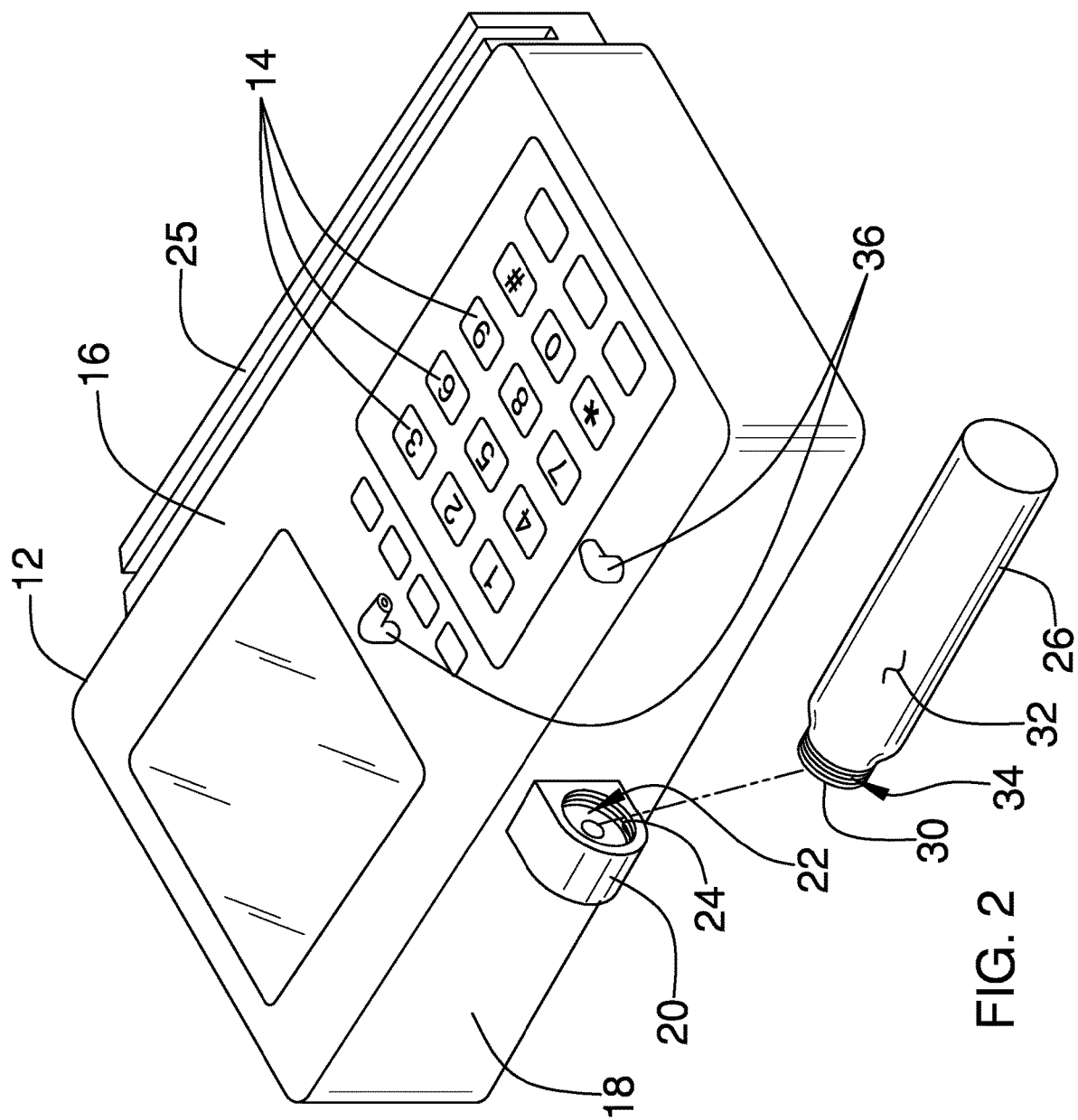
FIG. 2 is a perspective view of an embodiment of the disclosure showing a reservoir being coupled to a fluid port.
Figure 3:
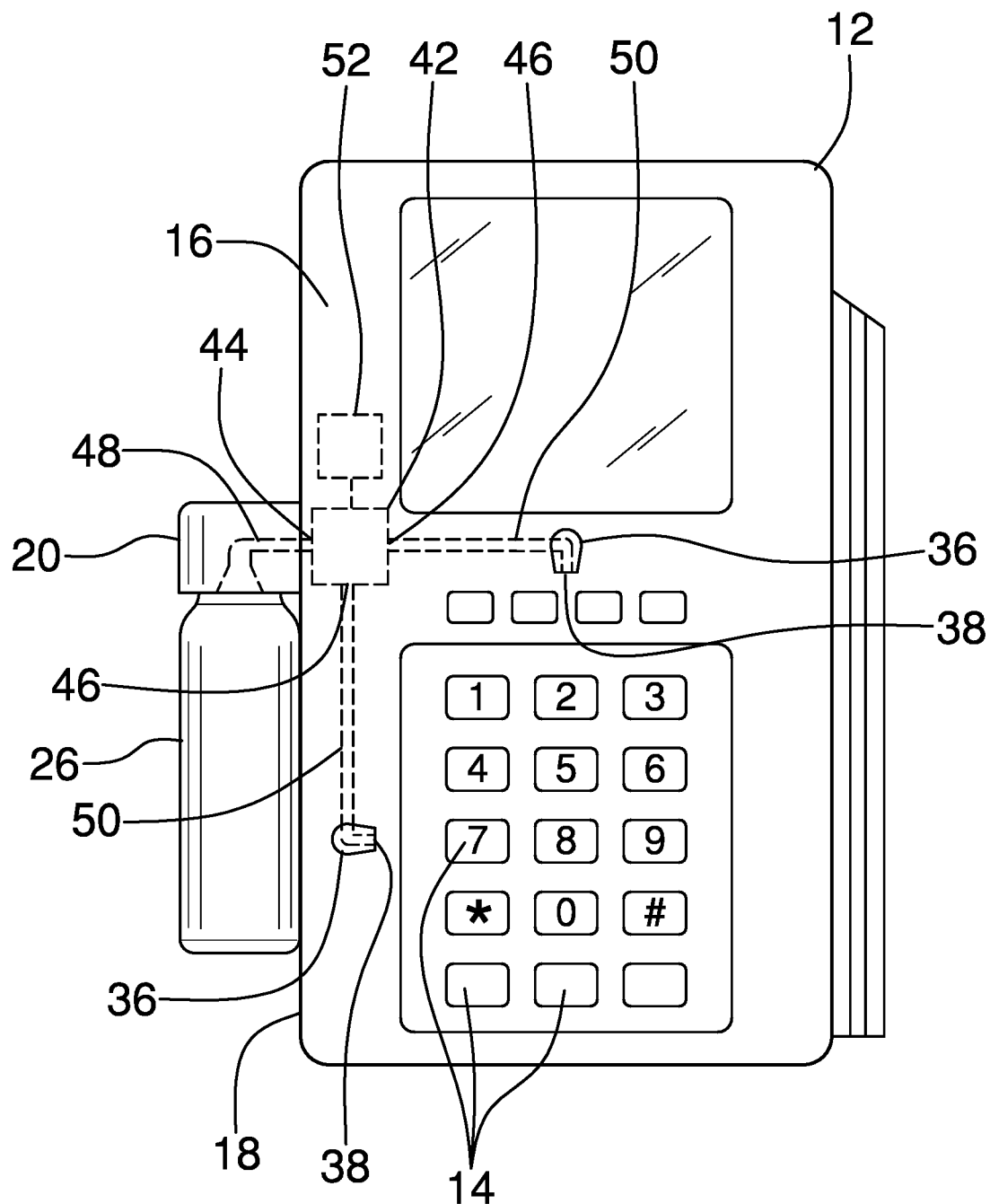
FIG. 3 is a top phantom view of an embodiment of the disclosure.
Figure 4:
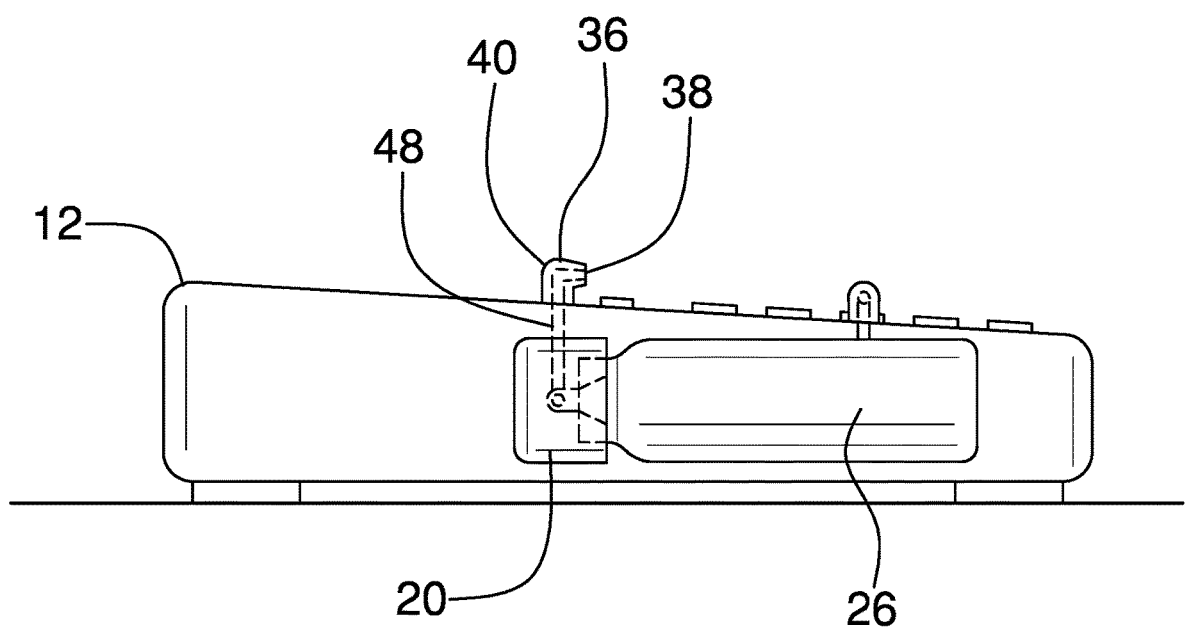
FIG. 4 is a left side phantom view of an embodiment of the disclosure.
Figure 5:
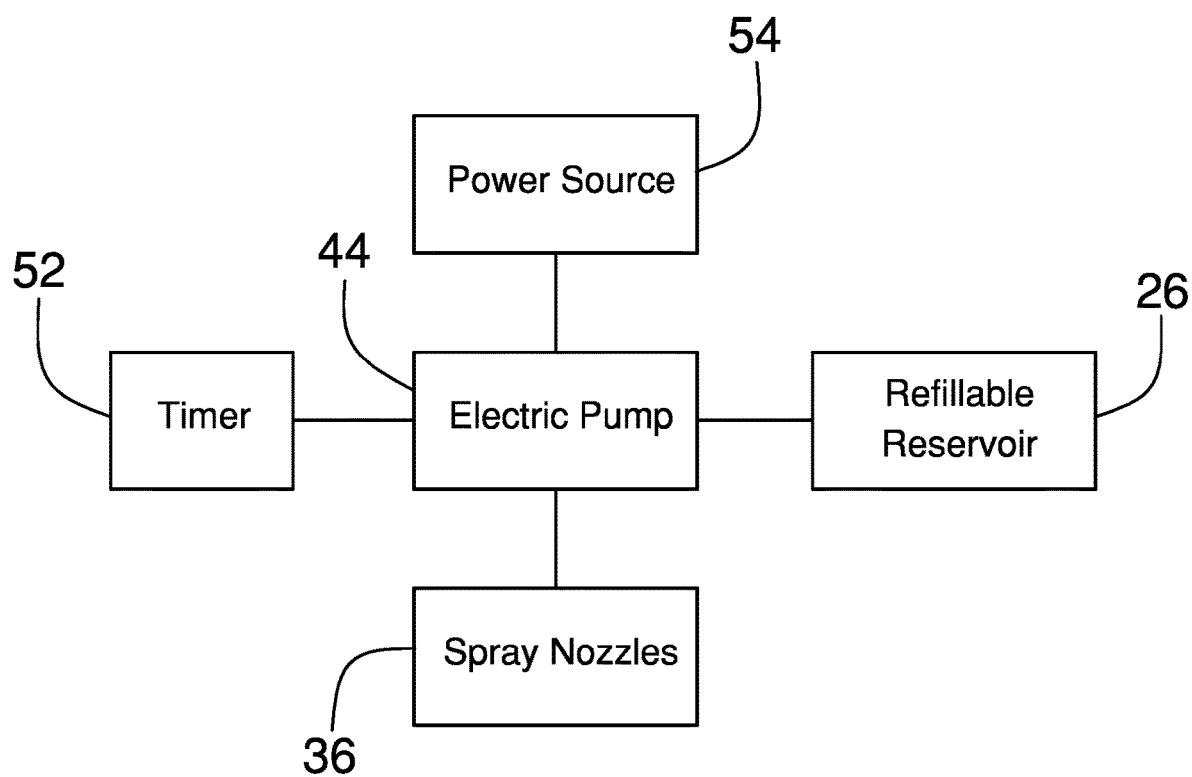
FIG. 5 is a schematic view of an embodiment of the disclosure.

With reference now to the drawings, and in particular to FIGS. 1 through 5 thereof, a new sterilization device embodying the principles and concepts of an embodiment of the disclosure and generally designated by the reference numeral 10 will be described.

As best illustrated in FIGS. 1 through 5, the keypad sterilization assembly 10 generally comprises a keypad 12 that has a plurality of keys 14 movably integrated therein for entering an alpha-numeric code. The keypad 12 has a top side 16 and a first lateral side 18, and each of the keys 14 is positioned on the top side 16. The keypad 12 might be a keypad at a point of sale machine, a keypad on an automated teller machine or any other keypad that would typically be touched by a large number of people. A fluid port 20 is coupled to the keypad 12 and the fluid port 20 is positioned on the first lateral side 18 of the keypad 12. The fluid port 20 has a well 22 extending inwardly into the fluid port 20, the well 22 has a bounding surface 24 and the bounding surface 24 is threaded. The keypad 12 may include a card reader 25 for reading a credit card or debit card that is swiped through the card reader 25.

A reservoir 26 is provided that is fluidly attachable to the fluid port 20 and the reservoir 26 contains an anti-bacterial solution 28. The anti-bacterial solution 28 may be a fluid sanitizer that is approved for use on human skin. The reservoir 26 has an outlet 30 and an outer surface 32, and the outer surface 32 has a threaded portion 34 adjacent to the outlet 30. The threaded portion 34 threadably engages the bounding surface 24 of the well 22 such that the outlet 30 is in fluid communication with the fluid port 20 thereby facilitating the fluid port 20 to receive the anti-bacterial solution 28. The reservoir 26 may be a cylinder or other elongated container that can fit in a streamlined manner on the first lateral side 18 of the keypad 12. The reservoir 26 can be refilled with any desired type of anti-bacterial solution.

A pair of nozzles 36 is provided and each of the nozzles 36 is coupled to the keypad 12. Each of the nozzles 36 is directed toward the plurality of keys 14 and each of the nozzles 36 is in fluid communication with the fluid port 20. Each of the nozzles 36 sprays a measured amount of the anti-bacterial solution 28 onto the keys 14 thereby facilitating the keys 14 to be sterilized. In this way keypad 12 in inhibited from contributing to contact transmission of infectious diseases between the large number of people that touch the keypad 12.

Each of the nozzles 36 is positioned on the top side 16 of the keypad 12 and each of the nozzles 36 has a distal end 38 with respect to the nozzles 36. The distal end 38 of each of the nozzles 36 is open and each of the nozzles 36 has a bend 40 positioned thereon. In this way the distal end 38 of each of the nozzles 36 is directed toward the top side 16 of the keypad 12. A pump 42 is positioned within the keypad 12 and the pump 42 has an inlet port 44 and a pair of outlet ports 46. The pump 42 may comprise an electric fluid pump or the like. Each of the nozzles 36 may be positioned adjacent to respective sides of the keys 14 on the keypad 12. Moreover, the nozzles 36 are oriented to have a direction of spray that is oriented perpendicular to each other. Thus, the nozzles 36 are oriented to evenly distribute the anti-bacterial solution 28 over all of the plurality of keys 14.

A supply conduit 48 is fluidly coupled between the fluid port 20 and the inlet port 44 such that the supply conduit 48 directs the anti-bacterial solution 28 to the inlet port 44. A pair of nozzle conduits 50 is each fluidly coupled between a respective one of the outlet ports 46 on the pump 42 and a respective one of the nozzles 36. The pump 42 urges the anti-bacterial solution 28 inwardly through the supply conduit 48 and outwardly through each of the nozzle conduits 50 when the pump 42 is turned on. In this way the anti-bacterial solution 28 is sprayed through each of the nozzles 36 to sterilize the keys 14 on the keypad 12.

A timer 52 is positioned within the keypad 12 and the timer 52 is electrically coupled to the pump 42. The timer 52 turns on the pump 42 for a predetermined duration of time over regularly scheduled intervals to maintain sterility of the keypad 12. The timer 52 may comprise an electronic timer or the like. Additionally, the predetermined duration of time may at least 2.0 seconds such that the pump 42 is able to deliver a sufficient volume of the anti-bacterial solution 28 to sterilize the keypad 12. A power supply 54 is positioned in the keypad 12, the power supply 54 is electrically coupled to the pump 42 and the power supply 54 may comprise an electrical system of the building in which the keypad 12 is positioned, or the power supply 54 may comprise a battery.

In use, the reservoir 26 is screwed into the fill port and the timer 52 turns on the pump 42 at regularly scheduled intervals. In this way a measured amount of the anti-bacterial solution 28 is sprayed onto the keypad 12 to sterilize the keypad 12. Additionally, the keypad 12 is continually sterilized over the course of a day such that the large number of people who employ the keypad 12 are inhibited from transmitting infectious diseases on the keypad 12. Thus, the keypad 12 does not contribute to an ongoing pandemic or other public health crisis that involves infectious diseases.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A keypad sterilization assembly for sterilizing a keypad at regularly scheduled intervals, said assembly comprising:
   a keypad having a plurality of keys being movably integrated therein wherein said plurality of keys is configured to be manipulated to entering an alphanumeric code;
   a fluid port being coupled to said keypad;
   a reservoir being fluidly attachable to said fluid port, said reservoir containing an anti-bacterial solution; and
   a pair of nozzles, each of said nozzles being coupled to said keypad, each of said nozzles being directed toward said plurality of keys, each of said nozzles being in fluid communication with said fluid port, each of said nozzles spraying a measured amount of said anti-bacterial solution onto said keys wherein said keys are configured to be sterilized.

2. The assembly according to claim 1, wherein:
   said keypad has a top side and a first lateral side, each of said keys being positioned on said top side;
   said fluid port is positioned on said first lateral side of said keypad, said fluid port having a well extending inwardly into said fluid port, said well having a bounding surface, said bounding surface being threaded; and
   said reservoir has an outlet and an outer surface, said outer surface having a threaded portion adjacent to said outlet, said threaded portion threadably engaging said bounding surface of said well such that said outlet is in fluid communication with said fluid port thereby facilitating said fluid port to receive the anti-bacterial solution.

3. The assembly according to claim 1, wherein each of said nozzles is positioned on a top side of said keypad, each of said nozzles having a distal end with respect to said nozzles, said distal end of each of said nozzles being open, each of said nozzles having a bend positioned thereon such that said distal end of each of said nozzles is directed toward said top side of said keypad.

4. The assembly according to claim 3, further comprising:
   a pump being positioned within said keypad, said pump having an inlet port and a pair of outlet ports;

a supply conduit being fluidly coupled between said fluid port and said inlet port such that said supply conduit directs said anti-bacterial solution to said inlet port; and a pair of nozzle conduits, each of said nozzle conduits being fluidly coupled between a respective one of said outlet ports on said pump and a respective one of said nozzles, said pump urging said anti-bacterial solution inwardly through said supply conduit and outwardly through each of said nozzle conduits when said pump is turned on thereby spraying said anti-bacterial solution through each of said nozzles.

5. The assembly according to claim 4, further comprising a timer being positioned within said keypad, said timer being electrically coupled to said pump, said timer turning on said pump for a predetermined duration of time over regularly scheduled intervals wherein said timer is configured to maintain sterility of said keypad.

6. A keypad sterilization assembly for sterilizing a keypad at regularly scheduled intervals, said assembly comprising:

a keypad having a plurality of keys being movably integrated therein wherein said plurality of keys is configured to be manipulated to entering an alphanumeric code, said keypad having a top side and a first lateral side, each of said keys being positioned on said top side;

a fluid port being coupled to said keypad, said fluid port being positioned on said first lateral side of said keypad, said fluid port having a well extending inwardly into said fluid port, said well having a bounding surface, said bounding surface being threaded;

a reservoir being fluidly attachable to said fluid port, said reservoir containing an anti-bacterial solution, said reservoir having an outlet and an outer surface, said outer surface having a threaded portion adjacent to said outlet, said threaded portion threadably engaging said bounding surface of said well such that said outlet is in fluid communication with said fluid port thereby facilitating said fluid port to receive the anti-bacterial solution;

a pair of nozzles, each of said nozzles being coupled to said keypad, each of said nozzles being directed toward said plurality of keys, each of said nozzles being in fluid communication with said fluid port, each of said nozzles spraying a measured amount of said anti-bacterial solution onto said keys wherein said keys are configured to be sterilized, each of said nozzles being positioned on said top side of said keypad, each of said nozzles having a distal end with respect to said nozzles, said distal end of each of said nozzles being open, each of said nozzles having a bend positioned thereon such that said distal end of each of said nozzles is directed toward said top side of said keypad;

a pump being positioned within said keypad, said pump having an inlet port and a pair of outlet ports;

a supply conduit being fluidly coupled between said fluid port and said inlet port such that said supply conduit directs said anti-bacterial solution to said inlet port;

a pair of nozzle conduits, each of said nozzle conduits being fluidly coupled between a respective one of said outlet ports on said pump and a respective one of said nozzles, said pump urging said anti-bacterial solution inwardly through said supply conduit and outwardly through each of said nozzle conduits when said pump is turned on thereby spraying said anti-bacterial solution through each of said nozzles;

a timer being positioned within said keypad, said timer being electrically coupled to said pump, said timer turning on said pump for a predetermined duration of time over regularly scheduled intervals wherein said timer is configured to maintain sterility of said keypad; and a power supply being positioned in said keypad, said power supply being electrically coupled to said pump, said power supply comprising an electrical system of the building in which said keypad is positioned.

* * * * *